(12) United States Patent
Ito et al.

(10) Patent No.: US 8,455,001 B2
(45) Date of Patent: *Jun. 4, 2013

(54) CELLULOSE DERIVATIVE AND METHOD FOR PRODUCTION THEREOF

(75) Inventors: Masaya Ito, Hino (JP); Hiroaki Kaneko, Hino (JP); Yukako Fukuhira, Hino (JP); Nobuyuki Endo, Hino (JP)

(73) Assignee: Teijin Limited, Osaka (JP)

( * ) Notice: Subject to any disclaimer, the term of this patent is extended or adjusted under 35 U.S.C. 154(b) by 556 days.

This patent is subject to a terminal disclaimer.

(21) Appl. No.: 12/525,464

(22) PCT Filed: Feb. 6, 2008

(86) PCT No.: PCT/JP2008/052382
§ 371 (c)(1),
(2), (4) Date: Jul. 31, 2009

(87) PCT Pub. No.: WO2008/096894
PCT Pub. Date: Aug. 14, 2008

(65) Prior Publication Data
US 2010/0129452 A1    May 27, 2010

(30) Foreign Application Priority Data

Feb. 6, 2007 (JP) ............................ 2007-026514
Feb. 6, 2007 (JP) ............................ 2007-026515
Apr. 4, 2007 (JP) ............................ 2007-098447

(51) Int. Cl.
*A61K 47/36* (2006.01)
*A61K 31/715* (2006.01)
*C08B 1/00* (2006.01)
*C08B 3/00* (2006.01)
*C08B 5/00* (2006.01)
*C08B 7/00* (2006.01)
*C08B 13/00* (2006.01)

(52) U.S. Cl.
USPC ................ 424/488; 514/57; 536/56; 536/62

(58) Field of Classification Search
USPC ........................ 424/488; 514/57; 536/56, 62
See application file for complete search history.

(56) References Cited

U.S. PATENT DOCUMENTS

| | | | |
|---|---|---|---|
| 5,064,817 A | * | 11/1991 | Yedgar et al. ................. 514/78 |
| 5,366,755 A | * | 11/1994 | Timonen et al. ............. 426/658 |
| 2002/0049183 A1 | * | 4/2002 | Yedgar et al. ................. 514/54 |
| 2007/0020314 A1 | | 1/2007 | Haro et al. |

FOREIGN PATENT DOCUMENTS

| | | |
|---|---|---|
| AU | 2006276435 A1 | 2/2007 |
| JP | 01-301624 A | 12/1989 |
| JP | 02-070703 A | 3/1990 |
| JP | 09-296005 | 11/1997 |
| JP | 2003-528026 A | 9/2003 |
| JP | 2005-508827 A | 4/2005 |
| JP | 2006-296916 A | 11/2006 |
| WO | 92/00105 | 1/1992 |
| WO | 92/20349 | 11/1992 |
| WO | WO9958168 A1 * | 11/1999 |
| WO | 01/46265 | 6/2001 |
| WO | 2005/000374 A1 | 1/2005 |
| WO | 2007/015579 A1 | 2/2007 |

OTHER PUBLICATIONS

JP 2006-296916 A, Teijin Ltd., machine translation obtained from JPO, Sep. 13, 2011 (8 pages).*
URL information for JP 2006-296916 A, JPO, Sep. 13, 2011 (1 page).*
JP 01-301624 A, partial translation, translation of portions cited on ISR; USPTO translation services, Sep. 15, 2011 (1 page).*
WO 2007/015579 A1, translation provided by the Australian Patent Office (link provided by WIPO website); Jan. 30, 2008 (31 pages).*
Translators Café. Com [downloaded Sep. 27, 2011] [Retrieved from internet <URL: http:// http://www.translatorscafe.com/cafe/units-converter/pressure/calculator/dyne-per-square-centimeter-%5Bdyn/cm%5E2%5D-to-newton-per-square-meter-%5BN/m%5E2%5D/>](1 page).*
B/373 International Preliminary Report on Patentability, Chapter I of PCT (Aug. 11, 2009) (English Translation);(7 pages).*
Written Opinon of the International Search Authority (English Translation) (Aug. 6, 2009) (6 pages).*
Teijin (JP 2006-296916 A; translation provided and cited in prior office action).*

Ryan et al., "Evaluation of Carboxymethylcellulose Sponge for Prevention of Postoperative Adhesions," *The American Journal of Surgery*, vol. 169, Jan. 1995, pp. 154-160.

\* cited by examiner

*Primary Examiner* — Jason M Sims
*Assistant Examiner* — Miriam A Levin
(74) *Attorney, Agent, or Firm* — Sughrue Mion, PLLC

(57) ABSTRACT

The invention provides a cellulose derivative having a repeating unit of the formula below, a composition including the cellulose derivative and a phospholipid, a method for production thereof, and an adhesion barrier including the cellulose derivative or the composition.

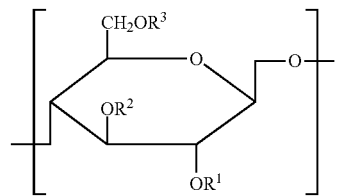

In the formula, $R^1$, $R^2$, and $R^3$ are —H, —$CH_2$—COOH, —$CH_2$—COOX, or —$CH_2$CO-phosphatidylethanolamine, and X is an alkali metal or an alkali earth metal. The degree of substitution of —$CH_2$—COOH and —$CH_2$—COOX is 0.3 to 2.0 in total, and the degree of substitution of —$CH_2$CO-phosphatidylethanolamine is 0.001 to 0.05.

26 Claims, 1 Drawing Sheet

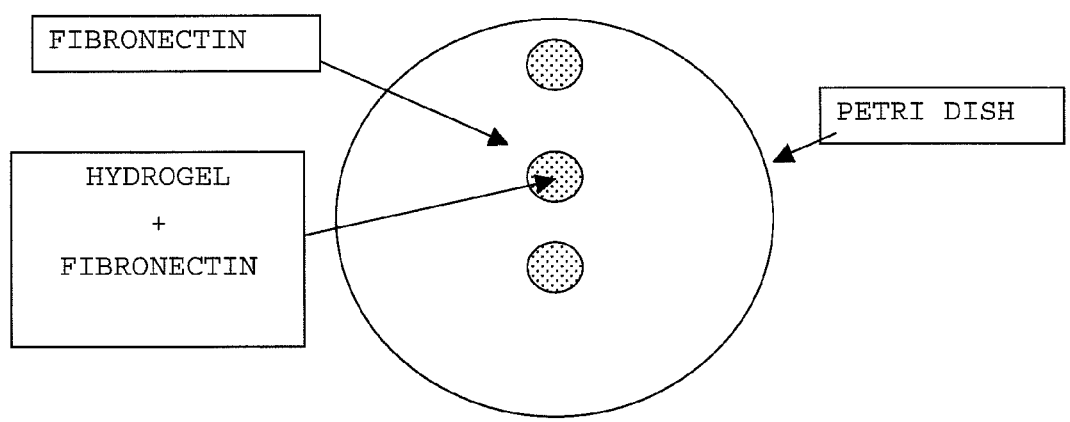

CELLULOSE DERIVATIVE AND METHOD FOR PRODUCTION THEREOF

PRIORITY CLAIM AND CROSS REFERENCE TO RELATED APPLICATIONS

This application is a U.S. National Stage application filed under 35 U.S.C. §371 of International Application No. PCT/JP2008/052382, filed on Feb. 6, 2008, in Japan, and published as WO 2008/096894 A1, in Japanese on Aug. 14, 2008, and claims priority under 35 U.S.C. §§119 and 365 to JP 2007/026514, JP 2007/026515, and JP 2007/098447, filed on Feb. 6, 2007, Feb. 6, 2007, and Apr. 4, 2007, respectively, in the Japanese Patent Office, and published in Japanese, the entire disclosures of which are incorporated herein by reference.

TECHNICAL FIELD

The present invention relates to a cellulose derivative of a specific structure, a composition including a cellulose derivative of a specific structure and a phospholipid, a method for production thereof, and an adhesion barrier including the cellulose derivative or the composition.

BACKGROUND ART

Adhesions of body tissues occur as the damaged organ surface binds to other tissues during the process of regeneration. In this connection, various kinds of adhesion barriers have been proposed that use biocompatible materials, such as cellulose and other polysaccharides, to prevent postoperative adhesions.

For example, an adhesion barrier using an aqueous solution of carboxymethylcellulose has been proposed (Am. J. Surg., 169, 154-159 (1995)). However, the adhesion barrier described in this publication has poor retention in the body, and cannot exhibit its adhesion barrier effect sufficiently. Accordingly, various attempts have been made to modify the polysaccharides using various methods, or make the polysaccharides water-insoluble.

For example, an adhesion barrier is proposed in which hyaluronic acid and carboxymethyl cellulose are modified with a carbodiimide (International Publication WO92/000105, and International Publication WO92/020349). Further, an adhesion barrier is proposed whose primary component is a cellulose derivative prepared by substituting the hydrogen atoms of cellulose with specific substituents (JP-A-1-301624). An adhesion barrier is also proposed that is formed from a hyaluronic acid compound modified with phosphatidylethanolamine (JP-A-2006-296916).

U.S. Pat. No. 5,064,817 describes obtaining phospholipase $A_2$ inhibiting compositions by the reaction of a low-molecular-weight carboxymethylcellulose with phosphatidylethanolamine in an aqueous solvent. It has been shown, however, that the intended compound cannot be obtained under the conditions of this reaction, as will be described later in Comparative Example 5.

International Publication WO2001/046265 describes a water-insoluble biocompatible gel prepared by the reaction of a polyanionic polysaccharide with an activating agent in an aqueous solution containing a water-miscible organic solvent, using, for example, carboxymethylcellulose as the polyanionic polysaccharide.

However, all of these proposals require further studies in regard to adhesion barrier effect, ease of handling, and safety. As noted above, there has been a suggestion to introduce a phospholipid into cellulose; however, no studies have been made concerning hydrogels that are easy to handle, and have an adhesion barrier effect.

JP-A-9-296005 describes introducing a hydrophobic modifying group to polysaccharides to increase viscosity and improve biostability without gelation of the polysaccharides. However, the publication does not describe or even indicate a cellulose derivative or a cellulose derivative-containing composition, such as that of the present invention, useful to provide the adhesion barrier effect.

DISCLOSURE OF THE INVENTION

An object of the present invention is to provide a cellulose derivative, or a composition including the same, useful as medical materials. Specifically, the invention provides a cellulose derivative, or a composition including the same, that can be provided as a hydrogel having an appropriate elastic modulus and viscoelasticity useful as adhesion barrier, and particularly a gel-like adhesion barrier having superior retention in the body. It is another object of the present invention to provide a method for producing such a cellulose derivative or a composition including the same.

The inventors of the present invention conducted intensive studies to provide a composition having an appropriate viscoelasticity and an improved adhesion barrier effect. In an effort to improve the viscoelasticity and therefore retention in the body, the inventors modified cellulose with a safe material. As a result, it was found that a novel cellulose derivative having an appropriate viscoelasticity useful as adhesion barrier, and that can form a hydrogel injectable through a syringe can be obtained when the hydrogen atoms on the side chains of carboxymethylcellulose are partially substituted with phosphatidylethanolamine, a substance found in the body. The inventors of the present invention also found that a cellulose derivative composition having an appropriate viscoelasticity and useful as adhesion barrier can be obtained when a specific amount of phospholipid is contained in the cellulose derivative.

Specifically, the present invention is a cellulose derivative having a repeating unit of the formula

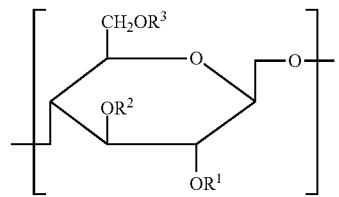

where $R^1$, $R^2$, and $R^3$ are independently selected from the group consisting of (a), (b), (c), and (d) below, —H                                                                  (a)

—$CH_2$—COOH                            (b)

—$CH_2$—COOX                            (c)

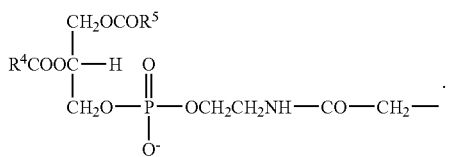

(d)

X in (c) is an alkali metal or an alkali earth metal.

$R^4$ and $R^5$ in (d) are independently an alkyl group or an alkenyl group having 9 to 27 carbon atoms.

The degree of substitution of (b) and (c) is 0.3 to 2.0 in total.

The degree of substitution of (d) is 0.001 to 0.05. The degree of substitution, as that term is used herein, refers to the number of each type of substituent when the total equivalent of (a), (b), (c), and (d) is 3.

Further, the present invention is a cellulose derivative composition which includes the cellulose derivative above and a phospholipid of the following formula

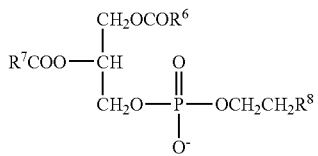

where $R^6$ and $R^7$ are independently an alkyl group or an alkenyl group having 9 to 27 carbon atoms, and $R^8$ is $-NH_3^+$ or $-N(CH_3)_3^+$.

Further, the present invention is a method for producing a cellulose derivative of the present invention, the method including dissolving:

a carboxymethylcellulose having a molecular weight of $5 \times 10^3$ to $5 \times 10^6$, and a repeating unit of the formula

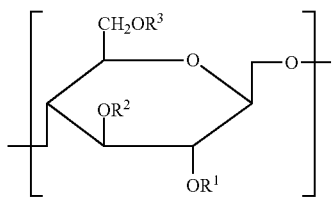

and a phosphatidylethanolamine of the formula

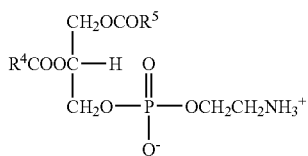

in a mixed solvent of 20 to 70 volume % water and a water-miscible organic solvent, so as to cause a reaction, in the presence of a condensing agent, between the carboxymethylcellulose and the phosphatidylethanolamine in such proportions that the phosphatidylethanolamine is 0.1 to 100 equivalents with respect to 100 equivalents of the carboxyl group of the carboxymethylcellulose.

$R^1$, $R^2$, and $R^3$ are independently selected from (a), (b), and (c) below, —H (a)

—$CH_2$—COOH (b)

—$CH_2$—COOX (c)

where X in (c) is an alkali metal or an alkali earth metal.

The degree of substitution of (b) and (c) is 0.3 to 2.0 in total.

$R^4$ and $R^5$ are independently an alkyl group or an alkenyl group having 9 to 27 carbon atoms.

Further, the present invention is a method for producing the cellulose derivative composition above, the method including:

mixing a cellulose derivative obtained by the method above, and a phospholipid of the formula

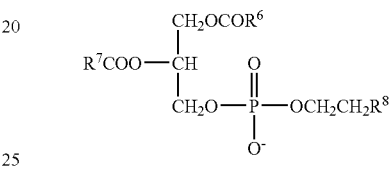

where $R^6$ and $R^7$ are independently an alkyl group or an alkenyl group having 9 to 27 carbon atoms, and $R^8$ is $-NH_3^+$ or $-N(CH_3)_3^+$, using a mixed solvent that contains water and a water-miscible organic solvent; and removing the solvent.

Further, the present invention is an adhesion barrier which includes the cellulose derivative or the cellulose derivative composition.

Further, the present invention is an injectable hydrogel which includes 0.1 to 1.5 parts by weight of the cellulose derivative with respect to 100 parts by weight of water.

Further, the present invention is an injectable hydrogel which includes 0.1 to 5.0 parts by weight of the cellulose derivative composition with respect to 100 parts by weight of water.

A cellulose derivative of the present invention forms a hydrogel having an appropriate elastic modulus and viscoelasticity. The cellulose derivative is colorless and transparent, and has a viscoelasticity sufficient to form a gel even at low concentrations. Further, the cellulose derivative is injectable with an instrument having a narrow tube, such as a syringe. A cellulose derivative of the present invention can be efficiently produced by a producing method of the present invention.

A cellulose derivative composition of the present invention, when dissolved in water, forms a hydrogel having an appropriate elastic modulus and viscoelasticity, and therefore can be used as an injectable gel or an adhesion barrier in medical applications. A cellulose derivative composition of the present invention contains a biological substance, phosphatidylethanolamines or phosphatidylcholines, and is therefore safe to use. A cellulose derivative composition of the present invention can form a hydrogel having an appropriate elastic modulus and viscoelasticity upon addition of free phosphatidylethanolamines or phosphatidylcholines to a cellulose derivative substituted with a phosphatidylethanolamine. A cellulose derivative composition of the present invention can be efficiently produced by a producing method of the present invention.

An adhesion barrier of the present invention has superior retention in the body, and exhibits an excellent adhesion barrier effect. A gel-like adhesion barrier of the present invention has a sufficient flexibility and viscoelasticity, and is easy to handle, making it applicable to complexly shaped areas, and to surgeries that use an endoscope.

BRIEF DESCRIPTION OF THE DRAWINGS

FIG. 1 is a schematic illustration showing a fibronectin-coated petri dish, together with a hydrogel plus fibronectin drop.

BEST MODE FOR CARRYING OUT THE INVENTION

<Cellulose Derivative>

The present invention is a cellulose derivative having a repeating unit of the formula

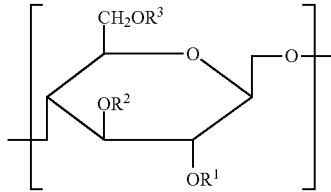

where $R^1$, $R^2$, and $R^3$ are independently selected from the group consisting of (a), (b), (c), and (d) below.

—H  (a)

—CH$_2$—COOH  (b)

—CH$_2$—COOX  (c)

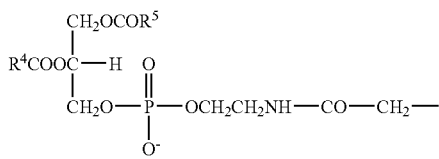
(d)

(The stereoisomerism for the asymmetric carbons in (d) is not particularly limited.)

X in (c) is an alkali metal or an alkali earth metal.

$R^4$ and $R^5$ in (d) are independently an alkyl group or an alkenyl group having 9 to 27 carbon atoms.

The degree of substitution of (b) and (c) is 0.3 to 2.0 in total.

The degree of substitution of (d) is 0.001 to 0.05.

The alkali metal represented by X is preferably an element such as sodium, potassium, or lithium, and the alkali earth metal is preferably an element such as magnesium or calcium.

$R^4$ and $R^5$ in (d) are preferably alkenyl groups having 9 to 19 carbon atoms. Specifically, $R^4$CO— and/or $R^5$CO— are preferably oleoyl groups, and particularly preferably $R^4$CO— and $R^5$CO— are oleoyl groups.

The degree of substitution of (b) and (c) is 0.3 to 2.0, preferably 0.5 to 1.8, more preferably 0.6 to 1.5 in total. The proportions of (b) and (c) are not particularly limited. However, considering solubility in water, it is preferable that (c) be in excess of (b).

The degree of substitution of (d) is 0.001 to 0.05, preferably 0.005 to 0.03. With the degree of substitution of (d) controlled in this range, a gel can be obtained that has an appropriate viscoelasticity, and that can be injected with an instrument having a narrow tube, such as a syringe. The degree of substitution of (d) is determined by the elemental quantitative analysis of phosphorus. The elemental analysis of phosphorus can be performed by measuring free phosphorus ions after the hydrolysis of a cellulose derivative in an appropriate acidic aqueous solution, using absorption spectrometry based on colors produced by, for example, a phosphorus-molybdenum method, or using an emission analysis such as IPC.

A cellulose derivative of the present invention has a weight average molecular weight of preferably $5\times10^3$ to $5\times10^6$, more preferably $5\times10^4$ to $5\times10^6$, further preferably $5\times10^4$ to $1\times10^6$. Because the weight average molecular weight of the cellulose derivative increases by the introduction of the group represented by (d), a cellulose derivative of a target molecular weight can be obtained by appropriately selecting the molecular weight of the raw material carboxymethylcellulose.

<Cellulose Derivative Composition>

The present invention is a cellulose derivative composition that contains the cellulose derivative and a phospholipid of the formula

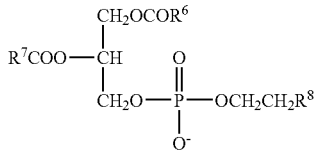

where $R^6$ and $R^7$ are independently an alkyl group or an alkenyl group having 9 to 27 carbon atoms, and $R^8$ is —NH$_3^+$ or —N(CH$_3$)$_3^+$.

The molar equivalent ratio of the repeating unit of the cellulose derivative to the phospholipid is 1:0.05 to 1:1.

The constituent cellulose derivative of a cellulose derivative composition of the present invention is preferably those described as being preferable in conjunction with a cellulose derivative of the present invention.

Specifically, the alkali metal represented by X is preferably an element such as sodium, potassium, and lithium, and the alkali earth metal is preferably an element such as magnesium and calcium. $R^4$ and $R^5$ in (d) are preferably alkenyl groups having 9 to 19 carbon atoms. Specifically, $R^4$CO— and/or $R^5$CO— are preferably oleoyl groups, and particularly preferably $R^4$CO— and $R^5$CO— are oleoyl groups.

$R^6$ and $R^7$ in the phospholipid of the formula above are preferably alkenyl groups having 9 to 19 carbon atoms. Specifically, $R^6$CO— and/or $R^7$CO— are preferably oleoyl groups, and particularly preferably $R^6$CO— and $R^7$CO— are oleoyl groups.

$R^8$ is preferably —NH$_3^+$.

In a cellulose derivative composition of the present invention, it is preferable that $R^4$, $R^5$, $R^6$, and $R^7$ are the same. It is particularly preferable that $R^4$CO—, $R^5$CO—, $R^6$CO—, and $R^7$CO— are oleoyl groups. Most preferably, $R^4$CO—, $R^5$CO—, $R^6$CO—, and $R^7$CO— are oleoyl groups, and $R^8$ is —NH$_3^+$.

<Producing Method of Cellulose Derivative>

A cellulose derivative of the present invention can be produced by a method that includes dissolving:

a carboxymethylcellulose having a molecular weight of $5\times10^3$ to $5\times10^6$, and a repeating unit of the formula

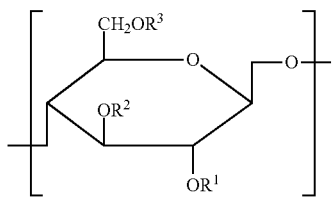

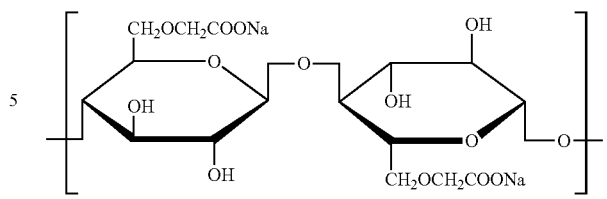

and a phosphatidylethanolamine of the formula

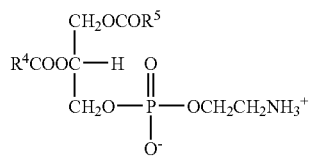

in a mixed solvent of 20 to 70 volume % water and a water-miscible organic solvent, so as to cause a reaction, in the presence of a condensing agent, between the carboxymethylcellulose and the phosphatidylethanolamine in such proportions that the phosphatidylethanolamine is 0.1 to 100 equivalents with respect to 100 equivalents of the carboxyl group (a total of substituents (b) and (c)) of the carboxymethylcellulose.

$R^1$, $R^2$, and $R^3$ are independently selected from (a), (b), and (c) below, —H (a)

—CH$_2$—COOH (b)

—CH$_2$—COOX (c)

where X in (c) is an alkali metal or an alkali earth metal.

The degree of substitution of (b) and (c) is 0.3 to 2.0 in total.

$R^4$ and $R^5$ are independently an alkyl group or an alkenyl group having 9 to 27 carbon atoms.

The raw material carboxymethylcellulose has a molecular weight of preferably $5 \times 10^3$ to $5 \times 10^6$, more preferably $5 \times 10^4$ to $5 \times 10^6$, further preferably $5 \times 10^4$ to $1 \times 10^6$.

The raw material carboxymethylcellulose can be produced by, for example, dissolving pulp in a sodium hydroxide solution, and purifying it by etherification with monochloroacetic acid or a sodium salt thereof.

The alkali metal represented by X in (c) is preferably an element such as sodium, potassium, and lithium, and the alkali earth metal is preferably an element such as magnesium and calcium.

The degree of substitution of (b) and (c) is 0.3 to 2.0, preferably 0.5 to 1.8, more preferably 0.6 to 1.5 in total. The proportions of (b) and (c) are not particularly limited. However, considering solubility in water, it is preferable that (c) be in excess of (b).

Specifically, the preferable structural formula of the raw material carboxymethylcellulose is as shown below. The substitution position of the carboxymethyl group on the cellulose backbone is preferably C-6.

In the phosphatidylethanolamine of the formula above used in a cellulose derivative producing method of the present invention, $R^4$ and $R^5$ are independently an alkyl group or an alkenyl group having 9 to 27 carbon atoms. $R^4$ and $R^5$ are preferably alkenyl groups having 9 to 27 carbon atoms. Specifically, $R^4$CO— and/or $R^5$CO— are preferably oleoyl groups, and particularly preferably $R^4$CO— and $R^5$CO— are oleoyl groups.

The raw material phosphatidylethanolamine may be extracted from animal tissue, or may be synthesized. Examples of the phosphatidylethanolamine include: dilauroyl phosphatidylethanolamine, dimyristoyl phosphatidylethanolamine, dipalmitoyl phosphatidylethanolamine, distearoyl phosphatidylethanolamine, diarachidoyl phosphatidylethanolamine, dibehenoyl phosphatidylethanolamine, dilignoceroyl phosphatidylethanolamine, dicerotoyl phosphatidylethanolamine, dimontanoyl phosphatidylethanolamine, lauroleoyl phosphatidylethanolamine, myristoleoyl phosphatidylethanolamine, palmitoleoyl phosphatidylethanolamine, dioleoyl phosphatidylethanolamine, dinervonoyl phosphatidylethanolamine, dilinoleoyl phosphatidylethanolamine, dilinolenoyl phosphatidylethanolamine, dihiragonoyl phosphatidylethanolamine, diarachidonoyl phosphatidylethanolamine, and didocosahexaenoyl phosphatidylethanolamine. Among these, dioleoyl phosphatidylethanolamine is preferable considering solubility in the organic solvent used for the synthesis.

It is believed that phosphatidylethanolamine, a safe biological substance, enhances the hydrophobic interaction between the molecules of a cellulose derivative of the present invention, and that a cellulose derivative of the present invention forms a hydrogel as a result of these hydrophobic interactions.

The reaction between the raw material carboxymethylcellulose and phosphatidylethanolamine of a cellulose derivative of the present invention is performed in such proportions that the phosphatidylethanolamine is 0.1 to 100 equivalents, preferably 0.2 to 50 equivalents, more preferably 0.3 to 40 equivalents with respect to 100 equivalents of the carboxyl group of the carboxymethylcellulose. When the amount of phosphatidylethanolamine is less than 0.1 equivalents, the product cellulose derivative does not form a hydrogel. An amount in excess of 100 equivalents is not preferable because it increases the hydrophobicity of the product cellulose derivative, and encourages the formation of insolubles. In the condensation reaction of the carboxymethylcellulose and the phosphatidylethanolamine, because the reaction efficiency may be reduced depending on the reactivity of the catalyst used in the condensation, or by the reaction conditions, it is preferable that the phosphatidylethanolamine be used in excess of the amount calculated for the target degree of substitution.

The carboxymethylcellulose and the phosphatidylethanolamine are dissolved in a mixed solvent of 20 to 70 volume % water and water-miscible organic solvent (A). A water content below 20 volume % makes it difficult to dissolve the carboxymethylcellulose. Above 70 volume %, it becomes difficult to dissolve the phosphatidylethanolamine. In either case, the reaction does not proceed. The preferable water content is 30 to 60 volume %.

Specific examples of the water-miscible organic solvent (A) include: organic solvents having a cyclic ether bond, such as tetrahydrofuran, 1,4-dioxane, 1,3-dioxane, 1,3-dioxolan, and morpholine; organic solvents having an amide bond, such as dimethylacetoamide, dimethylformamide, and N-methyl-2-pyrrolidone; amines such as pyridine, piperidine, and piperazine; and sulfoxides such as dimethyl sulfoxide. Among these, cyclic ethers and sulfoxides are preferable, and tetrahydrofuran, dioxane, and dimethyl sulfoxide are more preferable.

The condensing agent used for the reaction is preferably a carboxyl activating agent or a condensing agent (in the narrow sense). Examples of the carboxyl activating agent include N-hydroxysuccinimide, p-nitrophenol, N-hydroxybenzotriazole, N-hydroxypiperidine, N-hydroxysuccinamide, 2,4,5-trichlorophenol, and N,N-dimethylaminopyridine. Examples of the condensing agent (in the narrow sense) include 1-ethyl-3-(dimethylaminopropyl)-carbodiimide or hydrochloric acid salts thereof, diisopropylcarbodiimide, dicyclohexylcarbodiimide, and N-hydroxy-5-norbornene-2,3-dicarboxylmide. Among these, the preferable carboxyl activating agent is N-hydroxybenzotriazole, and the preferable condensing agent (in the narrow sense) is a hydrochloric acid salt of 1-ethyl-3-(dimethylaminopropyl)-carbodiimide.

The preferable reaction temperature is 0° C. to 60° C. Preferably, the reaction is performed at 0° C. to 10° C. to prevent formation of by-products. The preferable reaction environment is weakly acidic, more preferably a pH of 6 to 7.

<Purification Method of Cellulose Derivative>

A cellulose derivative producing method of the present invention may include the step of purifying the product cellulose derivative with organic solvent (B) that is water-miscible and essentially does not dissolve the carboxymethylcellulose.

As used herein, the phrase "essentially does not dissolve the carboxymethylcellulose" means that the organic solvent hardly dissolves the carboxymethylcellulose in the absence of water, as measured by the solubility of a sodium salt of carboxymethylcellulose or a carboxymethylcellulose (COOH form) available as a powder or a freeze-dried product. Specifically, it refers to organic solvents having a solubility of 3% or less. Examples include: alcohols such as methanol, ethanol, n-propyl alcohol, isopropyl alcohol, n-butyl alcohol, and t-butyl alcohol; polyalcohols such as ethylene glycol, 1,2-propylene glycol, 1,3-propylene glycol, and glycerin; ketones such as acetone; and aromatic alcohols such as phenol. Among these, the preferred organic solvents are those having a boiling point of less than 100° C., more preferably a boiling point of 73.8° C. or less. Preferred examples include methanol, ethanol, and isopropyl alcohol. Considering use in the body, ethanol is preferable.

When purifying the cellulose derivative with these groups of organic solvent (B), the cellulose derivative may be removed as a precipitate formed by adding organic solvent (B) to the cellulose derivative contained in a mixture of water and organic solvent (A). Alternatively, the cellulose derivative may be removed by adding organic solvent (B) and washing the precipitate obtained as above, or a dry powder or a freeze-dried, shaped article such as a sponge. These purification methods can remove the condensing agent, such as the carboxyl activating agent, and the catalysts used for the reaction, and the unreacted phospholipids remaining in the reaction system. The target products suspended in organic solvent (B) are separated by a method such as centrifugation or filtration. Soxhlet extraction can be used for the washing with organic solvent (B).

<Producing Method of Cellulose Derivative Composition>

A cellulose derivative composition of the present invention can be produced by a method that includes:

mixing a cellulose derivative produced by the foregoing method, and a phospholipid of the formula

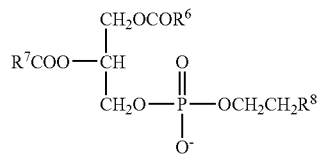

where $R^6$ and $R^7$ are independently an alkyl group or an alkenyl group having 9 to 27 carbon atoms, and $R^8$ is $-NH_3^+$ or $-N(CH_3)_3^+$, using a mixed solvent that contains water and a water-miscible organic solvent; and removing the solvent.

Specifically, the phospholipid used in the foregoing step is selected from phosphatidylethanolamines or phosphatidylcholines. $R^6$ and $R^7$ are independently an alkyl group or an alkenyl group having 9 to 27 carbon atoms. It is preferable that $R^6$ and $R^7$ are alkenyl groups having 9 to 19 carbon atoms. Specifically, $R^6CO-$ and/or $R^7CO-$ are preferably oleoyl groups, and particularly preferably $R^6CO-$ and $R^7CO-$ are oleoyl groups.

The phospholipid may be extracted from animal tissue, or may be synthesized. Examples of the phosphatidylethanolamine include dilauroyl phosphatidylethanolamine, dimyristoyl phosphatidylethanolamine, dipalmitoyl phosphatidylethanolamine, distearoyl phosphatidylethanolamine, diarachidoyl phosphatidylethanolamine, dibehenoyl phosphatidylethanolamine, dilignoceroyl phosphatidylethanolamine, dicerotoyl phosphatidylethanolamine, dimontanoyl phosphatidylethanolamine, lauroleoyl phosphatidylethanolamine, myristoleoyl phosphatidylethanolamine, palmitoleoyl phosphatidylethanolamine, dioleoyl phosphatidylethanolamine, dinervonoyl phosphatidylethanolamine, dilinoleoyl phosphatidylethanolamine, dilinolenoyl phosphatidylethanolamine, dihiragonoyl phosphatidylethanolamine, diarachidonoyl phosphatidylethanolamine, and didocosahexaenoyl phosphatidylethanolamine.

Examples of the phosphatidylcholine include dilauroyl phosphatidylcholine, dimyristoyl phosphatidylcholine, dipalmitoyl phosphatidylcholine, distearoyl phosphatidylcholine, diarachidoyl phosphatidylcholine, dibehenoyl phosphatidylcholine, dilignoceroyl phosphatidylcholine, dicerotoyl phosphatidylcholine, dimontanoyl phosphatidylcholine, lauroleoyl phosphatidylcholine, myristoleoyl phosphatidylcholine, palmitoleoyl phosphatidylcholine, dioleoyl phosphatidylcholine, dinervonoyl phosphatidylcholine, dilinoleoyl phosphatidylcholine, dilinolenoyl phosphatidylcholine, dihiragonoyl phosphatidylcholine, diarachidonoyl phosphatidylcholine, and didocosahexaenoyl phosphatidylcholine.

Among these, dioleoyl phosphatidylethanolamine and dioleoyl phosphatidylcholine are particularly preferable.

The cellulose derivative and the phospholipid are mixed in a mixed solvent containing water and water-miscible organic solvent (A). The mixed solvent is 20 to 70 volume % water, preferably 30 to 60 volume % water.

The organic solvent (A) may be those exemplified above. Cyclic ethers and sulfoxides are preferable. Tetrahydrofuran, dioxane, and dimethyl sulfoxide are more preferable.

In a cellulose derivative composition of the present invention, by mixing the cellulose derivative with the phospholipid, the viscoelasticity of the resulting composition, and the viscoelasticity of the hydrogel obtained upon addition of water can be increased. The mixture ratio of the cellulose derivative and the phospholipid is preferably 1:0.1 to 1:0.8, more preferably 1:0.15 to 1:0.6, based on the 1:0.05 to 1:1 molar equivalent ratio of the repeating unit of the cellulose derivative to the phospholipid. When the molar equivalent ratio of the phospholipid is below 0.05, there will be no improvement in viscoelasticity. Above 1, the phospholipid will simply be in excess, and the viscoelasticity improving effect is not usually observed.

The cellulose derivative is mixed with the phospholipid at a temperature of 0° C. to 30° C., preferably 10° C. to 25° C. The polymer and phospholipid content in the solvent is not particularly limited, and is preferably 3 weight % or less in total.

After mixing the cellulose derivative with the phospholipid, the organic solvent (A) is removed to obtain a target composition. The method of removing the organic solvent (A) is not particularly limited, and it can be removed by methods such as vacuum concentration, freeze-drying, and dialysis against water, or methods such as spray drying, electrospray deposition, and air-drying, or by precipitating a target product by addition of a low-solubility solvent. Among these, the method that removes the organic solvent by dialysis against water is preferable. It is also preferable to use a method that dries the resulting dialysate by freeze-drying. The dialysis membrane is not particularly limited, and a commercially available visking tube (regenerated cellulose film) can be suitably used.

<Hydrogel of Cellulose Derivative>

An adhesion barrier of the present invention is a hydrogel that contains a cellulose derivative of the present invention in an amount of 0.1 to 5.0 parts by weight, preferably 0.2 to 2.0 parts by weight, more preferably 0.3 to 1.0 part by weight with respect to 100 parts by weight of water.

The hydrogel preferably has a viscoelasticity high enough to prevent the hydrogel from flowing out of a tilted container. The hydrogel can easily undergo deformation upon contact with a metal spatula such as a spatel, and the state of the hydrogel is such that it can be readily applied to the affected area. Further, the hydrogel is injectable with an instrument having a narrow tube, such as a syringe.

The gel preferably has a complex elastic modulus of to 900 $N/m^2$, more preferably 100 to 700 $N/m^2$, as measured at an angular velocity of 10 rad/sec using a dynamic viscoelasticity measurement device under the conditions that the polymer concentration in water is 1 weight %, and the temperature is 37° C. Gels in these ranges are the easiest to handle in injection applications.

A hydrogel of the present invention is colorless and transparent. This is advantageous in terms of industrial production, because it allows for detection of dust or other foreign materials incorporated during the production.

The hydrogel may contain components other than water. Possible examples include condensing agents used as the catalysts; by-products, such as urea, generated by a predetermined chemical reaction of the condensing agents; the carboxyl activating agents; the unreacted phosphatidylethanolamines; foreign materials that may be incorporated in each stage of the reaction; and ions used to adjust pH. However, these components are removed by the purification or washing using the organic solvent (B), preferably to the extent that they will not elicit a foreign-body reaction in the body.

<Hydrogel of Cellulose Derivative Composition>

A cellulose derivative composition of the present invention can form a hydrogel. A hydrogel with an appropriate viscoelasticity can be obtained by including the cellulose derivative composition in an amount of 0.1 to 5.0 parts by weight, preferably 0.2 to 2.0 parts by weight, more preferably 0.3 to 1.0 part by weight with respect to 100 parts by weight of water.

The hydrogel preferably has a viscoelasticity high enough to prevent the hydrogel from flowing out of a tilted container. The hydrogel can easily undergo deformation upon contact with a metal spatula such as a spatel, and the state of the hydrogel is such that it can be readily applied to the affected area. Further, the hydrogel is injectable with an instrument having a narrow tube, such as a syringe.

The gel preferably has a complex elastic modulus of 50 to 900 $N/m^2$, more preferably 100 to 700 $N/m^2$, as measured at an angular velocity of 10 rad/sec using a dynamic viscoelasticity measurement device under the conditions that the polymer concentration in water is 1 weight %, and the temperature is 37° C. Gels in these ranges are the easiest to handle in injection applications.

The hydrogel may contain components other than water, the cellulose derivative, and the phospholipid. Possible examples include condensing agents used as the catalysts; by-products, such as urea, generated by a predetermined chemical reaction of the condensing agents; the carboxyl activating agents; foreign materials that may be incorporated in each stage of the reaction; and ions used to adjust pH. These components are preferably reduced to the extent that they will not elicit a foreign-body reaction in the body.

<Use>

A cellulose derivative, a cellulose derivative composition, and a hydrogel of the present invention have medical applications such as medical materials, or can be used to provide daily commodities such as haircare products and skin moisturizers. A use in cosmetic applications is also possible. The gel, injectable with a syringe, can be suitably used as medical materials in minimally invasive medical applications, such as a cell carrier in regenerative medicine, a carrier for the retention and sustained-release of liquid factors such as growth factors, a carrier for the retention and sustained-release of low molecular compounds usable as drugs, and an adhesion barrier or a sealant, particularly an injectable adhesion barrier.

EXAMPLES

The present invention is described below in more detail based on examples. It should be noted that the invention is in no way limited by the descriptions of the following examples.

(1) The following materials were used in the examples.

(i) CMC—Na: Sodium Carboxymethylcellulose (Nippon Paper Chemicals; the degree of substitution, 0.69)

(ii) Tetrahydrofuran (Wako Pure Chemical Industries, Ltd.)

(iii) 0.1 M HCl (Wako Pure Chemical Industries, Ltd.)

(iv) 0.1 M NaOH (Wako Pure Chemical Industries, Ltd.)

(v) EDC: 1-Ethyl-3-[3-(dimethylamino)propyl]-carbodiimide.HCl (Osaka Synthetic Chemical Laboratories, Inc.)

(vi) HOBt.$H_2O$: 1-Hydroxybenzotriazole, monohydrate (Osaka Synthetic Chemical Laboratories, Inc.)

(vii) L-α-dioleoyl phosphatidylethanolamine (COATSOME ME-8181, NOF Corporation)

(viii) L-α-dilauroyl phosphatidylethanolamine (COATSOME ME-2020, NOF Corporation)

(ix) L-α-dioleoyl phosphatidylcholine (COATSOME MC-8181, NOF Corporation)

(x) L-α-dilauroyl phosphatidylcholine (COATSOME MC-2020, NOF Corporation)

(xi) L-α-dimyristoyl phosphatidylcholine (COATSOME MC-4040, NOF Corporation)
(xii) L-α-dipalmitoyl phosphatidylcholine (COATSOME MC-6060, NOF Corporation)
(xiii) L-α-distearyl phosphatidylcholine (COATSOME MC-8080, NOF Corporation)
(xiv) Fibronectin (Becton, Dickinson and Company, Japan)
(xv) Nitrocellulose (Schleicher & Schuell)
(xvi) Mouse NIH/3T3 fibroblast (distributed from American Type Culture Collection)
(xvii) PBS (Invitrogen)
(xviii) DMEM (Invitrogen)
(xix) Antibiotics Antimycotics (Invitrogen)
(xx) FBS (Hyclone)
(xxi) Trypsin-EDTA: 0.25% trypsin, 1 mM EDTA.4Na (Invitrogen)
(xxii) Methanol (Wako Pure Chemical Industries, Ltd.)
(xxiii) Ethanol for disinfection (Wako Pure Chemical Industries, Ltd.)
(xxiv) Sodium pentobarbital (Nembutal injection, Dainippon Sumitomo Pharma Co., Ltd.)
(xxv) Isodine antiseptic (Meiji Seika)
(xxvi) Distilled water for injection (Otsuka Pharmaceutical Co., Ltd.)

(2) Measurement of Phospholipid Content in Cellulose Derivative

The proportion of the phospholipid in the cellulose derivative was determined by the analysis of the total phosphorus content using vanadomolybdate absorption spectrometry.

(3) Measurement of Complex Elastic Modulus of Hydrogel

The complex elastic modulus of the hydrogel was measured at 37° C. and an angular velocity of 10 rad/sec using a dynamic viscoelasticity measurement device (Rheometer RFS III; TA Instruments). Complex elastic modulus is a constant that represents a stress-to-strain ratio of an elastic body.

Example 1

Cellulose Derivative

Two hundred milligrams of CMC—Na having an average molecular weight of 2.3 million was dissolved in 40 ml of water, and 40 ml of tetrahydrofuran was added. Then, 169.7 mg of L-α-dioleoyl phosphatidylethanolamine (0.000228 mol; 40 equivalents with respect to 100 equivalents of the carboxyl group of CMC—Na), 48 mg of EDC (0.000251 mol), and 38.4 mg of HOBt.H$_2$O (0.000251 mol) were dissolved in 10 ml of the solution (tetrahydrofuran/water=1/1) to be added to the reaction system. After stirring the mixture overnight, the tetrahydrofuran was removed. The mixture was then added to ethanol to cause precipitation, after evaporating some of the water. The ethanol was removed by filtration, and, after re-washing with ethanol, the residue was vacuum dried to obtain a cellulose derivative. The phospholipid content in the cellulose derivative was then measured. The phospholipid content was used to calculate the degree of substitution of (d), based on assumptions that the degree of substitution of the sodium carboxymethyl cellulose before the reaction is 0.69, and that all the carboxymethyl groups have reacted with sodium. The degree of substitution of (d) was 0.007.

<Cellulose Derivative Composition>

One hundred milligrams of the cellulose derivative (0.45 mmol) obtained as above was dissolved in 20 ml of tetrahydrofuran/water=1/1, and 20.6 mg (0.028 mmol) of L-α-dioleoyl phosphatidylethanolamine was added to make the molar equivalent ratio of the repeating unit of the cellulose derivative to the L-α-dioleoyl phosphatidylethanolamine 1:0.062. The mixture was stirred for 20 hours, purified by dialysis, and freeze dried to obtain a cellulose derivative composition.

<Hydrogel of Cellulose Derivative>

Ten milligrams of a freeze-dried cellulose derivative was dissolved in 990 mg of ion-exchange water to prepare a 1 weight % hydrogel. The hydrogel was colorless and transparent, and did not flow even when the container was tilted. Further, the hydrogel allowed for easy insertion of a metal spatula such as a spatel. It was also possible to easily eject the hydrogel through a 25 G injection needle. The complex elastic modulus of the hydrogel was measured to be 188.2 N/m$^2$.

<Hydrogel of Cellulose Derivative Composition>

Ten milligrams of a freeze-dried cellulose derivative composition was dissolved in 990 mg of ion-exchange water to prepare a 1 weight % hydrogel. The complex elastic modulus of the hydrogel was measured to be 188.3 N/m$^2$.

Example 2

A hydrogel was prepared from a cellulose derivative composition obtained as in Example 1 except that 43.8 mg (0.059 mmol) of L-α-dioleoyl phosphatidylethanolamine was added to make the molar equivalent ratio of the repeating unit of the cellulose derivative to the L-α-dioleoyl phosphatidylethanolamine 1:0.13. The complex elastic modulus of the hydrogel was measured to be 287.3 N/m$^2$.

Example 3

A hydrogel was prepared from a cellulose derivative composition obtained as in Example 1 except that 89.6 mg (0.12 mmol) of L-α-dioleoyl phosphatidylethanolamine was added to make the molar equivalent ratio of the repeating unit of the cellulose derivative to the L-α-dioleoyl phosphatidylethanolamine 1:0.26. The complex elastic modulus of the hydrogel was measured to be 291.9 N/m$^2$.

Example 4

A hydrogel was prepared from a cellulose derivative composition obtained as in Example 1 except that 135.6 mg (0.18 mmol) of L-α-dioleoyl phosphatidylethanolamine was added to make the molar equivalent ratio of the repeating unit of the cellulose derivative to the L-α-dioleoyl phosphatidylethanolamine 1:0.40. The complex elastic modulus of the hydrogel was measured to be 308.9 N/m$^2$.

Example 5

A hydrogel was prepared from a cellulose derivative composition obtained as in Example 1 except that 231 mg (0.31 mmol) of L-α-dioleoyl phosphatidylethanolamine was added to make the molar equivalent ratio of the repeating unit of the cellulose derivative to the L-α-dioleoyl phosphatidylethanolamine 1:0.69. The complex elastic modulus of the hydrogel was measured to be 294.2 N/m$^2$.

Example 6

A hydrogel was prepared from a cellulose derivative composition obtained as in Example 1 except that 28.6 mg (0.036 mmol) of L-α-dioleoyl phosphatidylcholine was added to 30 mg (0.14 mmol) of the cellulose derivative used in Example 1 to make the molar equivalent ratio of the repeating unit of the cellulose derivative to the L-α-dioleoyl phosphatidylcholine 1:0.26. The complex elastic modulus of the hydrogel was measured to be 174.9 N/m².

Example 7

A hydrogel was prepared from a cellulose derivative composition obtained as in Example 6 except that 22.5 mg (0.036 mmol) of L-α-dilauroyl phosphatidylcholine was added to make the molar equivalent ratio of the repeating unit of the cellulose derivative to the L-α-dilauroyl phosphatidylcholine 1:0.27. The complex elastic modulus of the hydrogel was measured to be 249.1 N/m².

Example 8

A hydrogel was prepared from a cellulose derivative composition obtained as in Example 6 except that 24.6 mg (0.036 mmol) of L-α-dimyristoyl phosphatidylcholine was added to make the molar equivalent ratio of the repeating unit of the cellulose derivative to the L-α-dimyristoyl phosphatidylcholine 1:0.27. The complex elastic modulus of the hydrogel was measured to be 398.4 N/m².

Example 9

A hydrogel was prepared from a cellulose derivative composition obtained as in Example 6 except that 26.7 mg (0.036 mmol) of L-α-dipalmitoyl phosphatidylcholine was added to make the molar equivalent ratio of the repeating unit of the cellulose derivative to the L-α-dipalmitoyl phosphatidylcholine 1:0.27. The complex elastic modulus of the hydrogel was measured to be 244.8 N/m².

Example 10

A hydrogel was prepared from a cellulose derivative composition obtained as in Example 6 except that 28.8 mg (0.036 mmol) of L-α-distearoyl phosphatidylcholine was added to make the molar equivalent ratio of the repeating unit of the cellulose derivative to the L-α-distearoyl phosphatidylcholine 1:0.27. The complex elastic modulus of the hydrogel was measured to be 261.2 N/m².

Example 11

A hydrogel was prepared from a cellulose derivative composition obtained as in Example 6 except that 20.9 mg (0.036 mmol) of L-α-dilauroyl phosphatidylethanolamine was added to make the molar equivalent ratio of the repeating unit of the cellulose derivative to the L-α-dilauroyl phosphatidylethanolamine 1:0.27. The complex elastic modulus of the hydrogel was measured to be 212.7 N/m².

Example 12

Preparation of Mouse NIH/3T3 Fibroblasts

Mouse NIH/3T3 fibroblasts were cultured in DMEM containing 10% FBS and 1% Antibiotics Antimycotics in the presence of 5% $CO_2$. In in vitro evaluation of cell adhesion and invasion to the hydrogel, the mouse NIH/3T3 fibroblasts were separated from a tissue culturing petri dish with 0.05% trypsin-EDTA, and centrifuged at 900 rpm for 5 minutes at room temperature. The supernatant was removed, and suspended in DMEM containing 10% FBS and 1% Antibiotics Antimycotics to prepare a cell suspension of $0.4 \times 10^5$ cells/ml.

<Evaluation of Cell Adhesion and Invasion to Cellulose Derivative Composition Hydrogel>

Postoperative adhesions occur as the damaged organ surface binds to other tissues during regeneration. One way to prevent this is to prevent cell invasion to the damaged tissue. Thus, cell adhesion and invasion to the cellulose derivative composition hydrogel was evaluated using the method of Snow et al. with modification [Snow D M, Lemmon V, Carrino D A, Caplan A I, Silver J.: Exp. Neurol; 109(1): 111-30. 1990]. Specifically, a 5-cm² nitrocellulose was dissolved in 6 ml of methanol, and a tissue culturing petri dish (diameter, 60 mm) was coated with 0.5 ml of this solution and air-dried for 2 hours. The cellulose derivative composition hydrogel of Example 1 was dropped on the nitrocellulose-coated petri dish, and air-dried for 6 hours. The petri dish was then coated with 3 ml of fibronectin (30 μg/ml), and washed with PBS (FIG. 1). Finally, 5 ml of the mouse NIH/3T3 fibroblast suspension ($0.4 \times 10^5$ cells/ml) was seeded over the entire petri dish ($2 \times 10^5$ cells/petri dish). Cell adhesion and invasion to the hydrogel drop was observed for 7 days using a phase-contrast microscope. The observation did not detect any cell adhesion or invasion to the dropped cellulose derivative composition hydrogel.

Example 13

The procedure of Example 12 was performed, and cell adhesion and invasion to the hydrogel was evaluated as above, except that the hydrogel of Example 2 was used instead of the cellulose derivative composition hydrogel of Example 1. The result was essentially the same as that of Example 12.

Example 14

The procedure of Example 12 was performed, and cell adhesion and invasion to the hydrogel was evaluated as above, except that the hydrogel of Example 3 was used instead of the cellulose derivative composition hydrogel of Example 1. The result was essentially the same as that of Example 12.

Example 15

The procedure of Example 12 was performed, and cell adhesion and invasion to the hydrogel was evaluated as above, except that the hydrogel of Example 5 was used instead of the cellulose derivative composition hydrogel of Example 1. The result was essentially the same as that of Example 12.

Comparative Example 1

The procedure of Example 12 was performed, and cell adhesion and invasion to the fibronectin was evaluated as above, except that 30 μg/ml fibronectin was used instead of the cellulose derivative composition hydrogel of Example 1. The spread of the cells was observed throughout the dropped fibronectin.

In Comparative Example 1, the adhesion and invasion of the mouse NIH/3T3 fibroblasts occurred for 7 days. In contrast, in Examples 12, 13, 14, and 15, the adhesion and invasion of the mouse NIH/3T3 fibroblasts to the hydrogel of the present invention was hardly observed during the same time period, and the cells selectively adhered to the fibronectin region not covered with the hydrogel.

These results confirmed that the hydrogels evaluated in Examples 12, 13, 14, and 15 have the effect of preventing cell adhesion and invasion.

Example 16

Intraperitoneal Adhesion Test

Ten Sprague-Dawley (SD) rats (7 weeks of age, male; Charles River Laboratories Japan Inc.) were used to create an intraperitoneal adhesion model according to the method of Buckenmaier CC 3rd, et al. [Buckenmaier CC 3rd, Pusateri A E, Harris R A, Hetz S P: Am Surg. 65(3):274-82, 1999]. Specifically, each rat was immobilized face-up under anesthesia provided by the intraperitoneal administration of sodium pentobarbital. The abdomen was shaved, and disinfected with ethanol for disinfection. The surgical region was further disinfected with an isodine antiseptic, and an incision was made 3 to 4 cm along the median line of the abdomen to expose the cecum. A certain area (1 to 2 $cm^2$) of the exposed cecum was abraded with a sterilized gauze until petechial hemorrhages occurred. The cecum was placed back, and a defect was created on the opposing abdominal wall (8 mm×16 mm). Then, the cellulose derivative hydrogel (1 ml) of Example 1 was applied to the defect area of the abdominal wall, and the incised muscle layer was closed with a continuous suture, followed by 4 to 5 stitches to close the skin. The rats were put back in the cage after disinfecting the wound area with isodine antiseptic. After 4 weeks from the creation of the model, the abdomen of each animal was opened under sodium pentobarbital anesthesia, and the degree of intraperitoneal adhesions was grossly observed and scored according to the following criteria. The rat that had no cellulose derivative hydrogel was used as a control.
(Scores)
Score 0: No adhesion
Score 1: Weak adhesion breakable under a weak traction
Score 2: Medium strength adhesion that withstands a weak traction
Score 3: Very strong adhesion Statistical analysis was performed using the Wilcoxon's method.

In the control, the formation of strong adhesions was observed between the abdominal wall and the cecum after 4 weeks. In the group that had the hydrogel of Example 1, the degree of adhesion between the abdominal wall and the cecum after 4 weeks was significantly lower than that of the control. Specifically, there was a statistically significant difference between the control (mean±standard deviation of 2.3±1.2) and the hydrogel (Example 1) applied group (mean±standard deviation of 0.8±1.2) at P=0.014 (Wilcoxon's test).

In rats that had adhesion, a paper clip was attached to the cecum with a suture thread. The clip was pulled with a Metric Gauge (EW-93953-05; Cole-Parmer), and the maximum strength (grams) needed to detach the cecum from the abdominal wall was measured to evaluate the adhesion strength. The value of adhesion strength was zero in rats that had no adhesion. The significant difference was determined using Welch's t-test. The effect of the cellulose derivative hydrogel of Example 1 on the degree or strength of adhesion was evaluated in this manner. The result confirmed a statistically significant difference between the control (mean±standard deviation of 338.7±278.4 grams) and the cellulose derivative hydrogel (Example 1) applied group (mean±standard deviation of 108.1±188.7 grams) at P=0.044 (Welch's t test).

It was therefore confirmed that the cellulose derivative hydrogel of Example 1 is indeed capable of preventing adhesions.

Example 17

The procedure of Example 16 was performed except that eight rats were used with the cellulose derivative composition hydrogel of Example 1 instead of the cellulose derivative hydrogel of Example 1. The effect of the cellulose derivative composition hydrogel on the degree or strength of adhesion was then evaluated. The adhesion score and the strength were 0.1±0.4, and 18±52 grams (means±standard deviation), respectively.

Example 18

The procedure of Example 17 was performed except that nine rats were used with the hydrogel of Example 2 instead of the cellulose derivative composition hydrogel of Example 1. The effect of the hydrogel on the degree or strength of adhesion was then evaluated. The adhesion score and the strength were 0.2±0.7, and 50±149 grams (means±standard deviation), respectively.

Example 19

The procedure of Example 17 was performed except that eight rats were used with the hydrogel of Example 3 instead of the cellulose derivative composition hydrogel of Example 1. The effect of the hydrogel on the degree or strength of adhesion was then evaluated. The adhesion score and the strength were 0.0±0.0, and 0±0 grams (means±standard deviation), respectively. That is, adhesion was completely suppressed.

Example 20

The procedure of Example 17 was performed except that nine rats were used with the hydrogel of Example 5 instead of the cellulose derivative composition hydrogel of Example 1. The effect of the hydrogel on the degree or strength of adhesion was then evaluated. The adhesion score and the strength were 0.6±1.1, and 89±180 grams (means±standard deviation), respectively.

Comparative Example 2

As a control, the procedure of Example 17 was performed without applying the hydrogel, and the degree and strength of adhesion were evaluated. The adhesion score and the strength were 2.0±1.3, and 397±313 grams (means±standard deviation), respectively.

In Comparative Example 2, strong adhesions were observed after 4 weeks. In contrast, in Examples 17, 18, 19, and 20, the degree and strength of adhesion were significantly reduced.

These results confirmed that the cellulose derivative composition hydrogels obtained in Examples 1, 2, 3, and 5 of the present invention indeed have the effect of strongly suppressing adhesions in the body, showing that the hydrogels are capable of effectively preventing postoperative adhesions.

Table 1 below summarizes the results of Examples 17 to 20, and Comparative Example 2.

TABLE 1

| Groups | Adhesion score, Means ± standard deviation | Significant difference test against Com. Ex. 2 (Wilcoxon) | Adhesion strength (grams), Means ± standard deviation | Significant difference test against Com. Ex. 2 (Welch) |
|---|---|---|---|---|
| Com. Ex. 2 | 2.0 ± 1.3 | — | 397 ± 313 | — |
| Ex. 17 | 0.1 ± 0.4 | P = 0.007 | 18 ± 52 | P = 0.011 |
| Ex. 18 | 0.2 ± 0.7 | P = 0.006 | 50 ± 149 | P = 0.017 |
| Ex. 19 | 0.0 ± 0.0 | P = 0.003 | 0 ± 0 | P = 0.009 |
| Ex. 20 | 0.6 ± 1.1 | P = 0.034 | 89 ± 180 | P = 0.033 |

Example 21

The procedures of Examples 16 and 17 were performed except that the concentration and the applied amount of the cellulose derivative hydrogel of Example 1 were varied. The effect of the hydrogel on the degree or strength of adhesion was then evaluated. Nine rats were used in each group. The results are presented in Table 2.

TABLE 2

| Groups | Viscoelasticity Pa (10 rad/sec) | Adhesion score, Means ± standard deviation | Significant difference test against control group (Wilcoxon) | Adhesion strength (grams), Means ± standard deviation | Significant difference test against control group (Welch) |
|---|---|---|---|---|---|
| Control group | — | 1.89 ± 1.45 | — | 274.6 ± 231.2 | — |
| 0.5%, 1 mL | 80.8 | 0.00 ± 0.00 | 0.004 | 0.0 ± 0.0 | 0.007 |
| 1%, 1 mL | 122.6 | 0.44 ± 1.01 | 0.042 | 59.0 ± 155.8 | 0.036 |
| 2%, 1 mL | 590.7 | 0.11 ± 0.33 | 0.009 | 26.2 ± 78.7 | 0.012 |
| 1%, 0.25 mL | 122.6 | 0.00 ± 0.00 | 0.004 | 0.0 ± 0.0 | 0.007 |
| 1%, 0.5 mL | 122.6 | 0.33 ± 0.71 | 0.021 | 77.3 ± 186.8 | 0.065 |
| 1%, 2 mL | 122.6 | 0.00 ± 0.00 | 0.004 | 0.0 ± 0.0 | 0.007 |

At the same applied amount (1 ml), the degree and strength of adhesion were significantly lower than the control group at 0.5 weight % and greater. At the same concentration (1 weight %), the degree and strength of adhesion were also significantly lower than the control group even when the applied amount was as small as 0.25 ml. It was therefore confirmed that the hydrogel can exhibit desired effects in the body when used in these amounts and concentrations.

Example 22

The viscosity of the gel prepared by dissolving a cellulose derivative (prepared as in Example 1 except for using CMC—Na with a molecular weight of 970,000; degree of substitution 0.001; hereinafter "CMC-PE") in a sodium chloride aqueous solution was measured (Eta (P), measured at angular velocity of 10 rad/sec). The results are represented in Table 3. The polymer concentration is 1 weight %, and "CMC—Na" is the sodium carboxymethylcellulose (molecular weight of 970,000) used as the raw material. PBS denotes phosphate buffered saline (0.9% NaCl).

TABLE 3

| | Sodium chloride concentration (weight %) | | | | | |
|---|---|---|---|---|---|---|
| | 0.0 | 0.45 | 0.9 | 1.35 | 1.8 | PBS |
| CMC-PE | 5 | 73 | 74 | 60 | 82 | 86 |
| CMC-Na | 1 | — | 1 | — | — | 1 |

As shown in table 3, it was found, rather surprisingly, that the use of small amounts of sodium chloride with the cellulose derivative hydrogel of the present invention greatly increases the viscosity. The use of the hydrogel can be enhanced by taking advantage of this characteristic. For example, for injection applications, the hydrogel of the present invention can be injected in low viscosity form without addition of sodium chloride to make injection easier. At the site of administration, the hydrogel will be in contact with the body tissue, and the sodium chloride concentration and therefore the viscosity increase to help exhibit the desired effects of, for example, an adhesion barrier.

Comparative Example 3

The inventors of the present invention considered the viscoelasticity enhancing effect from the perspective of modification of other polysaccharides with hydrophobic groups having a primary amino group, in addition to a cellulose derivative hydrogel and a cellulose derivative composition hydrogel of the present invention. There was hardly any improvement in viscoelasticity in hydrogels prepared by modifying the carboxyl group of polysaccharides, for example, such as hyaluronic acid, with leucine methyl ester, tyrosine ethyl ester, phenylalanine methyl ester, vitamin K5, carbachol (carbamylcholine chloride), ethyl amine, and nicotinamide. In contrast, hydrogels modified with ethyl urea had a clear improvement in viscoelasticity. These findings suggest that the modification of polysaccharides with hydrophobic groups can improve the viscoelasticity of the hydrogel, but whether viscoelasticity is improved by which specific combination is difficult to predict.

Comparative Example 4

Evaluation was made as to the relationship between the viscoelasticity of the hydrogel obtained by modifying polysaccharides with hydrophobic groups and the adhesion barrier effect. A CMC-oleylamine derivative was prepared using a CMC—Na having an average molecular weight of 2.3 million according to the method of Example 1, except that oleylamine was used instead of phosphatidylethanolamine in equivalents with respect to 100 equivalents of the carboxyl group of the CMC—Na. The derivative had a complex elastic modulus of 87.4 N/m².

The inventors of the present invention have found that cellulose derivative hydrogels having a high viscoelasticity can also be obtained by modifying carboxymethylcellulose with alkylamine, specifically, oleylamine. However, the evaluation regarding cell adhesion and invasion to the hydrogel of Example 12 has revealed that the cell adhesion and invasion barrier effect of the CMC-alkylamine hydrogel is poor, and that the high viscoelasticity of the hydrogel does not always lead to a desirable adhesion barrier effect.

Comparative Example 5

In this comparative example, CMC—Na (F15MHC; degree of substitution 0.77; Nippon Paper Chemicals) was used. As the phospholipid, a dilauroyl phosphatidylethanolamine (COATSOME ME-2020, NOF Corporation) was used. The other reagents are as in Example 1.

One gram of CMC—Na was dissolved in 50 ml of water, and 200 mg of dilauroyl phosphatidylethanolamine was added to the solution, which was then stirred at room temperature for 1 hour. Then, 500 mg of EDC was added to the solution, and the mixture was stirred overnight at room temperature. The resulting solution was freeze dried after dialysis against deionized water. The freeze-dried product was then mixed with water to make the polymer concentration 1 weight %, and viscoelasticity was measured.

The complex elastic modulus of the freeze-dried product remained the same at 0.4 N/m² from the complex elastic modulus of CMC—Na before the reaction. That is, no change was observed in the property of the polymer solution before and after the reaction. The mixture of the cellulose derivative and water remained as a fluid, and flowed out of the container when it was tilted. There was no property attributable to the gel.

INDUSTRIAL APPLICABILITY

A cellulose derivative composition of the present invention is useful as a medical hydrogel, particularly an injectable adhesion barrier. The adhesion barrier can be used to prevent adhesions on the damaged surface of body tissue during spine, joint, tendon, nerve, or other surgeries. As a specific example, in spine surgeries, an adhesion barrier of the present invention can be applied to keep separate the dura mater from the surrounding nerve roots, and thereby prevent adhesions.

Any adhesion caused must be detached to remove pain or maintain movable regions. By being applied, an adhesion barrier of the present invention can prevent adhesions and thereby avoid second surgery, improving medical economy and the quality of patients' life.

Further, in gynecological surgery, an adhesion barrier of the present invention can be used in celiotomy, or in the uterine myomectomy with an endoscope. Adhesions can be prevented by applying an adhesion barrier of the present invention to the wound area after the surgery.

An adhesion barrier of the present invention has superior retention in the body, making it a useful adhesion barrier. Specifically, in a gel form, the adhesion barrier can be applied to complicated-shaped areas, and conveniently used in surgeries that use an endoscope.

The invention claimed is:

1. A cellulose derivative having a repeating unit of the formula

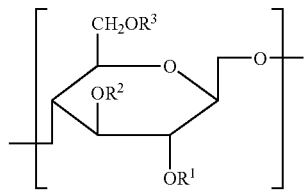

where $R^1$, $R^2$, and $R^3$ are independently selected from the group consisting of (a), (b), (c), and (d) below, —H                                                 (a)

—CH₂—COOH                         (b)

—CH₂—COOX                         (c)

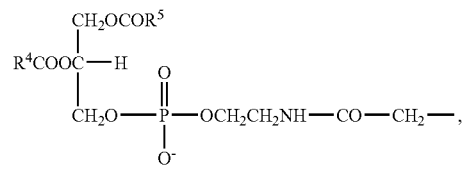

(d)

X in (c) being an alkali metal or an alkali earth metal, $R^4$ and $R^5$ in (d) being independently an alkenyl group having 9 to 19 carbon atoms, a degree of substitution of (b) and (c) being 0.3 to 2.0 in total, and a degree of substitution of (d) being 0.001 to 0.05, wherein the repeating unit can vary depending on its substituents, wherein $R^1$, $R^2$, and $R^3$ are not all hydrogen atoms in at least some repeating units.

2. The cellulose derivative according to claim 1, wherein a complex elastic modulus measured based on a 1 weight % aqueous solution at an angular velocity of 10 rad/sec using a dynamic viscoelasticity measurement device is 50 to 900 N/m², wherein the aqueous solution is composed only of the cellulose derivative and water.

3. The cellulose derivative according to claim 1, wherein $R^4CO$— and/or $R^5CO$— are oleoyl groups.

4. The cellulose derivative according to claim 1, wherein $R^4CO$— and $R^5CO$— are oleoyl groups.

5. A cellulose derivative composition which comprises a cellulose derivative of claim 1 and a phospholipid of the formula

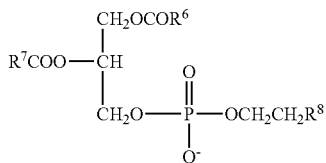

where $R^6$ and $R^7$ are independently an alkyl group or an alkenyl group having 9 to 27 carbon atoms, and $R^8$ is $-NH_3^+$ or $-N(CH_3)_3^+$, a molar equivalent ratio of the repeating unit of the cellulose derivative to the phospholipid being 1:0.05 to 1:1.

6. The cellulose derivative composition according to claim 5, wherein a complex elastic modulus measured based on a 1 weight % aqueous solution at an angular velocity of 10 rad/sec using a dynamic viscoelasticity measurement device is 50 to 900 N/m².

7. The cellulose derivative composition according to claim 5, wherein $R^8$ is $-NH_3^+$.

8. The cellulose derivative composition according to claim 5, wherein $R^8$ is $-N(CH_3)_3^+$.

9. The cellulose derivative composition according to claim 5, wherein $R^4$, $R^5$, $R^6$, and $R^7$ are all identical.

10. The cellulose derivative composition according to claim 5, wherein $R^6$ and $R^7$ are alkenyl groups having 9 to 19 carbon atoms.

11. The cellulose derivative composition according to claim 10, wherein $R^6CO-$ and/or $R^7CO-$ are oleoyl groups.

12. The cellulose derivative composition according to claim 10, wherein $R^6CO-$ and $R^7CO-$ are oleoyl groups.

13. The cellulose derivative composition according to any claim 5, wherein $R^4$ and $R^5$ are alkenyl groups having 9 to 19 carbon atoms.

14. The cellulose derivative composition according to claim 13, wherein $R^4CO-$ and/or $R^5CO-$ are oleoyl groups.

15. The cellulose derivative composition according to claim 13, wherein $R^4CO-$ and $R^5CO-$ are oleoyl groups.

16. The cellulose derivative composition according to claim 7, wherein $R^4CO-$, $R^5CO-$, $R^6CO-$, and $R^7CO-$ are all oleoyl groups.

17. A method for producing a cellulose derivative of claim 1, the method comprising dissolving:

a carboxymethyl cellulose having a molecular weight of $5\times10^3$ to $5\times10^6$, and a repeating unit of the formula

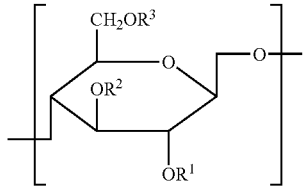

and
a phosphatidylethanolamine of the formula

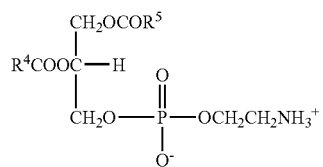

in a mixed solvent of 20 to 70 volume % water and a water-miscible organic solvent, so as to cause a reaction, in the presence of a condensing agent, between the carboxymethylcellulose and the phosphatidylethanolamine in such proportions that the phosphatidylethanolamine is 0.1 to 100 equivalents with respect to 100 equivalents of the carboxyl group of the carboxymethylcellulose, $R^1$, $R^2$, and $R^3$ being independently selected from (a), (b), and (c) below, $-H$ (a)

$-CH_2-COOH$ (b)

$-CH_2-COOX$ (c)

where X in (c) is an alkali metal or an alkali earth metal, a degree of substitution of (b) and (c) being 0.3 to 2.0 in total, and $R^4$ and $R^5$ being independently an alkenyl group having 9 to 19 carbon atoms, wherein the repeating unit can vary depending on its substituents, wherein $R^1$, $R^2$, and $R^3$ are not all hydrogen atoms in at least some repeating units.

18. The method according to claim 17, further comprising purifying the cellulose derivative after the reaction step, using a water-miscible organic solvent having a solubility of less than 3% for the carboxymethylcellulose, and a boiling point of less than 100° C.

19. The method according to claim 18, wherein the water-miscible organic solvent having a solubility of less than 3% for the carboxymethylcellulose, and a boiling point of less than 100° C. is ethanol.

20. The method according to claim 17, wherein the water-miscible organic solvent used in the reaction step is at least one selected from the group consisting of tetrahydrofuran, dioxane, and dimethyl sulfoxide.

21. A method for producing a cellulose derivative composition wherein the cellulose derivative composition comprises a cellulose derivative having a repeating unit of the formula

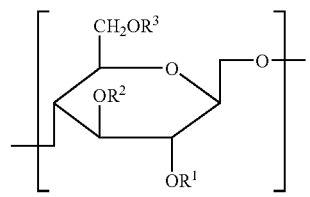

where $R^1$, $R^2$, and $R^3$ are independently selected from the group consisting of (a), (b), (c), and (d) below, $-H$ (a)

$-CH_2-COOH$ (b)

—CH$_2$—COOX  (c)

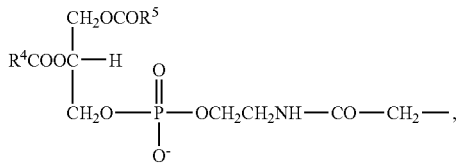
(d)

X in (c) being an alkali metal or an alkali earth metal,
R$^4$ and R$^5$ in (d) being independently an alkenyl group having 9 to 19 carbon atoms,
a degree of substitution of (b) and (c) being 0.3 to 2.0 in total, and
a degree of substitution of (d) being 0.001 to 0.05,
wherein the repeating unit can vary depending on its substituents,
wherein R$^1$, R$^2$, and R$^3$ are not all hydrogen atoms in at least some repeating units, and
a phospholipid,
the method comprising:
mixing a cellulose derivative obtained by a method of claim 18, and a phospholipid of the formula

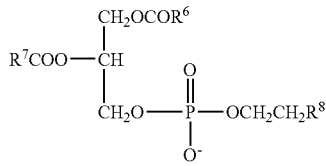

where R$^6$ and R$^7$ are independently an alkyl group or an alkenyl group having 9 to 27 carbon atoms, and R$^8$ is —NH$_3^+$ or —N(CH$_3$)$_3^+$, using a mixed solvent that contains water and a water-miscible organic solvent; and removing the solvent.

22. The method according to claim 21, wherein the solvent is removed by dialysis against water.

23. An adhesion barrier which comprises the cellulose derivative of claim 1.

24. An adhesion barrier which comprises a cellulose derivative composition of claim 5.

25. An injectable hydrogel which comprises 0.1 to 1.5 parts by weight of the cellulose derivative of claim 1 with respect to 100 parts by weight of water.

26. An injectable hydrogel which comprises 0.1 to 5.0 parts by weight of a cellulose derivative composition of claim 5 with respect to 100 parts by weight of water.

\* \* \* \* \*